US011271667B2

United States Patent
Kubo et al.

(10) Patent No.: US 11,271,667 B2
(45) Date of Patent: Mar. 8, 2022

(54) DATA RECEIVING APPARATUS, DATA TRANSMISSION APPARATUS AND DATA TRANSMISSION SYSTEM

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 149 days.

(21) Appl. No.: 16/747,628

(22) Filed: Jan. 21, 2020

(65) Prior Publication Data
US 2020/0153526 A1 May 14, 2020

Related U.S. Application Data

(63) Continuation of application No. PCT/JP2018/028824, filed on Aug. 1, 2018.

(30) Foreign Application Priority Data

Aug. 9, 2017 (JP) .............................. JP2017-154762

(51) Int. Cl.
*H04J 3/06* (2006.01)
*H04L 67/12* (2022.01)

(52) U.S. Cl.
CPC ............ *H04J 3/0664* (2013.01); *H04L 67/12* (2013.01)

(58) Field of Classification Search
None
See application file for complete search history.

(56) References Cited

U.S. PATENT DOCUMENTS 6,130,860 A    10/2000   Suzuki
2007/0171030 A1*   7/2007   Kobayashi .......... B60R 25/1004
                                                              340/426.1
(Continued)

FOREIGN PATENT DOCUMENTS

CN       1702697 A    11/2005
CN    105559753 A     5/2016
(Continued)

OTHER PUBLICATIONS

Official Communication issued in corresponding Chinese Patent Application No. 201880048283.3 dated Oct. 9, 2020.
(Continued)

*Primary Examiner* — Nicholas Sloms
(74) *Attorney, Agent, or Firm* — Keating and Bennett, LLP

(57) ABSTRACT

According an aspect of the present invention, a data receiving apparatus includes a calculator. The calculator (1) stores a date and time indicated by the clock unit in association with a first local date and time in the memory as a reference date and time, when the packet includes first date-and-time data indicating the first local date and time and information indicating that the first date-and-time data can be used for date and time association, and (2) calculates, when the packet includes sensor data and second date-and-time data indicating a second local date and time associated with the sensor data, a third date and time based on a difference between the first local date and time and the second local date and time, and on the reference date and time.

10 Claims, 7 Drawing Sheets

(56) References Cited

U.S. PATENT DOCUMENTS

| | | | | |
|---|---|---|---|---|
| 2011/0144506 A1* | 6/2011 | Kishimoto | ............ | G04R 20/08 600/490 |
| 2011/0294429 A1 | 12/2011 | Shirakata et al. | | |
| 2012/0016596 A1* | 1/2012 | Kubo | ................... | H04L 9/3231 702/19 |
| 2012/0302840 A1* | 11/2012 | Kubo | ..................... | G16H 10/60 600/300 |
| 2014/0028436 A1* | 1/2014 | Osako | ................... | G08C 19/00 340/3.2 |
| 2014/0232558 A1 | 8/2014 | Park et al. | | |
| 2015/0127284 A1* | 5/2015 | Seshan | .................. | G01D 21/00 702/89 |
| 2015/0335284 A1 | 11/2015 | Nuovo et al. | | |
| 2016/0029149 A1 | 1/2016 | Morikawa et al. | | |
| 2016/0041014 A1* | 2/2016 | Sameshima | .............. | G01D 3/10 702/127 |
| 2016/0150350 A1* | 5/2016 | Ingale | .................. | H04W 12/08 370/255 |
| 2016/0260301 A1* | 9/2016 | Miller | ................. | G06K 7/0008 |
| 2016/0307154 A1* | 10/2016 | Moore | ............... | G06Q 10/0838 |

FOREIGN PATENT DOCUMENTS

| | | | | |
|---|---|---|---|---|
| CN | 106102565 A | | 11/2016 | |
| EP | 2 994 900 A1 | | 3/2016 | |
| JP | 09-305888 A | | 11/1997 | |
| JP | 2008-183082 A | | 8/2008 | |
| JP | 2008-188379 A | | 8/2008 | |
| JP | 2008183082 | * | 8/2008 | ............ G06F 19/00 |
| JP | 2008-253480 A | | 10/2008 | |
| JP | 5852620 B2 | | 2/2016 | |
| WO | 2011/055477 A1 | | 5/2011 | |

OTHER PUBLICATIONS

Official Communication issued in International Patent Application No. PCT/JP2018/028824, dated Feb. 13, 2020.

Official Communication issued in International Patent Application No. PCT/JP2018/028824, dated Sep. 4, 2018.

Official Communication issued in corresponding Japanese Patent Application No. 2017-154762, dated Aug. 3, 2021.

* cited by examiner

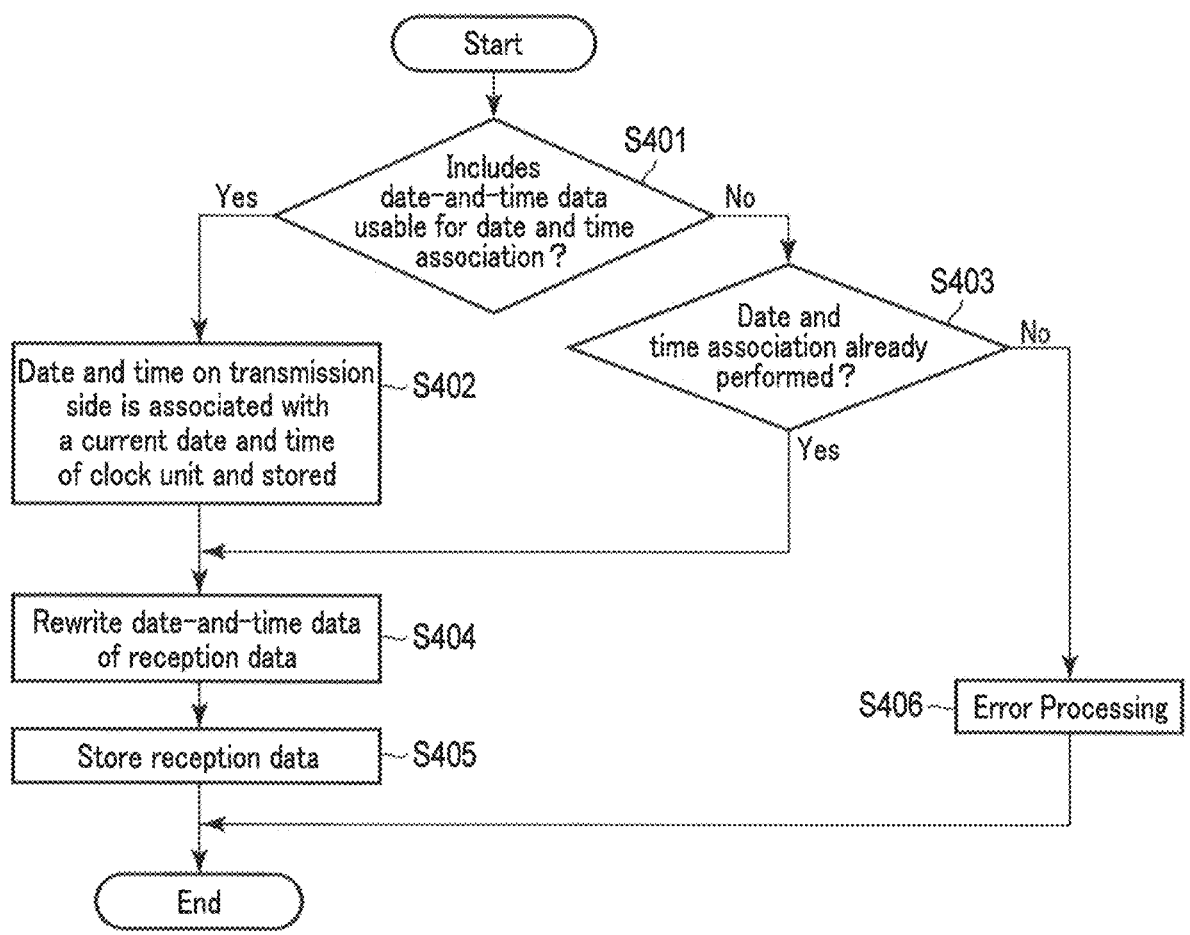
F I G. 5

FIG. 11

| User ID | latest flag | Time | Sys | Dia | Pulse |

FIG. 12

| Local date and time at transmitter side | Reference date and time at receiver side |
| 100[minutes] | 2017/04/01 9:00 |

FIG. 13

| Time | Sys | Dia | Pulse |
|---|---|---|---|
| 43300 | 136 | 86 | 74 |
| 43546 | 132 | 82 | 71 |
| 43789 | 129 | 79 | 69 |

⇩ Rewrite date-and-time data

| Time | Sys | Dia | Pulse |
|---|---|---|---|
| 2017/5/1 9:00 | 136 | 86 | 74 |
| 2017/5/1 13:06 | 132 | 82 | 71 |
| 2017/5/1 17:09 | 129 | 79 | 69 |

FIG. 14

DATA RECEIVING APPARATUS, DATA TRANSMISSION APPARATUS AND DATA TRANSMISSION SYSTEM

CROSS-REFERENCE TO RELATED APPLICATIONS

This application is a Continuation Application of PCT Application No. PCT/JP2018/028824, filed Aug. 1, 2018 and based upon and claiming the benefit of priority from Japanese Patent Application No. 2017-154762, filed Aug. 9, 2017, the entire contents of all of which are incorporated herein by reference.

FIELD

The present invention relates generally to a data receiving apparatus and a data transmission apparatus that transmit and receive sensor data associated with a date and time.

BACKGROUND

A blood pressure monitor with a function of transmitting blood pressure data to a portable information terminal of a user is on the market. Examples of the portable information terminal include a smartphone, a tablet terminal, and a notebook personal computer. When such a function is used, the user may be able to view its own blood pressure measurement result via a portable information terminal under various circumstances. Further, a short-range wireless communication technique, more specifically, Bluetooth (trademark registered) technique, is typically used during the transmission of blood pressure data. Generally, Bluetooth communication (connection) is achieved on a smaller scale and with greater power-saving compared to WLAN (Wireless Local Area Network) communication. Bluetooth specification version 4.0 is called BLE (Bluetooth Low Energy), and is characterized by its superior power-saving capabilities compared with prior specifications.

The BLE connection has its problems such as the complicated nature of the pairing operation that must be performed by the user, the complicated nature of the communication procedures after pairing, the smartphone needing to support BLE, the blood pressure monitor (and smartphone) needing high-performance hardware (processor, memory), the development/evaluation cost being high, the size of communication overhead being large, and its non-suitability for small-capacity data transmission.

On the other hand, BLE may perform one-way communication called advertising. Japanese Patent No. 5852620 discloses the technique of transmitting desired data by including it in a margin portion of the data field of the advertisement packet.

If the blood pressure data is transmitted using advertising, the process of pairing and other complex communication procedures becomes unnecessary, and the above problems may be largely solved. However, for example, if a blood pressure monitor implements only a one-way transmission function, the control data cannot be sent from the portable information terminal to the blood pressure monitor for control, and conversely, the state of the portable information terminal (such as the reception state of the data) cannot be referred to by the blood pressure monitor.

The blood pressure data is usually transferred from the blood pressure monitor to the portable information terminal in association with the data indicating the measurement date and time. The measurement date and time are given based on the date and time indicated by the built-in clock. Therefore, if the clock incorporated in the blood pressure monitor is incorrect, or the time is not adjusted in the first place, the portable information terminal processes the blood pressure data in association with the wrong measurement date and time. Even if it is detected that the measurement date and time is wrong, if the blood pressure monitor is equipped with only a one-way transmission function, it is impossible to adjust the clock incorporated in the blood pressure monitor by sending control data from the portable information terminal.

SUMMARY

According to a first aspect of the present invention, a data transmission system comprises a data transmission apparatus and a data receiving apparatus communicating with the data transmission apparatus. The data transmission apparatus includes: a first clock unit for indicating a date and time; and a transmitter for transmitting (1) a first packet for one-way communication including first date-and-time data indicating a date and time of the first clock unit and information indicating that the first date-and-time data can be used for the date and time association, and (2) a second packet for one-way communication including sensor data measured by a sensor and second date-and-time data indicating a date and time of the first clock unit at the measurement of the sensor data. The data receiving apparatus comprises: a second clock unit for indicating a date and time; a receiver for receiving the first packet and the second packet transmitted from the data transmission apparatus; and a calculator for (1) storing, in response to receipt of the first packet, a date and time indicated by the second clock unit in association with the date and time of the first clock unit shown by the first date-and-time data into a memory as a reference date and time, and (2) calculating, in response to receipt of the second packet, third date-and-time data based on a difference between the date and time stored in the memory and associated with the reference date and time and the date and time shown by the second date-and-time data, and on the reference date and time stored in the memory. Accordingly, in the data transmission system, the data receiving apparatus can, regardless of whether the date and time indicated by the second date-and-time data are correct or not, rewrite this date and time with reference to the date and time indicated by the own clock unit. In addition, the data receiving apparatus can prevent the accumulation of errors due to the difference in time counting between the clock unit in the sender of the packet and its own clock unit, by resetting the association between the reference date and time and the date and time in the sender of the packet. Also, in the data transmission system, the data transmission apparatus can advertise the date and time of its clock unit, and the information indicating that these date and time are usable for associating the date and time in the data receiving apparatus.

According to a second aspect of the present invention, a data receiving apparatus communicates with a data transmission apparatus. The data receiving apparatus comprises a clock unit for indicating a date and time; a receiver for receiving a packet for one-way communication transmitted from the data transmission apparatus; and a calculator for (1) storing, when the packet includes first date-and-time data showing a local date and time in the data transmission apparatus, and information indicating that the first date-and-time data is usable for date and time association, the date and time indicated by the clock unit in association with the local date and time shown by the first date-and-time data into a memory as a reference date and time, and (2) calculating, when the packet includes sensor data and second date-and-time data showing a local date and time in the data transmission apparatus and associated with the sensor data, third date-and-time data based on a difference between the local date and time stored in the memory and associated with the reference date and time and the local date and time shown by the second date-and-time data, and on the reference date and time stored in the memory. Therefore, in the data transmission system, the data receiving apparatus can rewrite the local date and time indicated by the second date-and-time data based on the date and time indicated by its own clock unit, regardless of whether the local date and time indicated by the second date-and-time data are correct or incorrect. In addition, the data receiving apparatus can prevent the accumulation of errors due to the difference in time counting between the clock unit in the sender of the packet and its own clock unit, by resetting the association between the reference date and time and the date and time in the sender of the packet.

According to a third aspect of the present invention, a data transmission apparatus comprises a clock unit for indicating a date and time, and a transmitter for transmitting (1) a first packet for one-way communication including first date-and-time data indicating a date and time of the clock unit and information indicating that the first date-and-time data can be used for the date and time association, and (2) a second packet for one-way communication including sensor data measured by a sensor and second date-and-time data indicating a date and time of the clock unit at the measurement of the sensor data. Therefore, the data transmission apparatus can advertise the date and time of its own clock unit, and the information indicating that these date and time can be used for associating the date and time in a data receiving apparatus.

According to a fourth aspect of the present invention, the transmitter transmits, before a predetermined time from the measurement date and time of the sensor data passes, the first packet including the sensor data, the first date-and-time data showing the date and time of the clock unit at the measurement of the sensor data, and information indicating that the first date-and-time data can be used for date and time association. The transmitter transmits, after the predetermined time from the measurement date and time of the sensor data passes, the second packet including the sensor data, the second date-and-time data showing the date and time of the clock unit at the measurement of the sensor data, and information indicating that the second date-and-time data is unusable for associating a date and time. Hence, the data transmission apparatus can advertise the sensor data, the date and time of its own clock unit at the measurement of the sensor data, and information indicating that the date and time can be used for associating the date and time in the data receiving apparatus, over a predetermined time period after the measurement of each piece of sensor data.

According to a fifth aspect of the present invention, the data transmission apparatus further comprises an input unit for receiving an input of operation information of a user, and the transmitter transmits the first packet including the first date-and-time data indicating the date and time of the clock unit, using a part of the operation information as a trigger. Thus, according to the data transmission apparatus, the user can intentionally advertise the date and time of the clock unit and the information indicating that the date and time can be used for associating the date and time in the data receiving apparatus.

According to a sixth aspect of the present invention, the data transmission apparatus is driven by a battery, and the transmitter transmits the first packet including the first date-and-time data indicating the date and time of the clock unit, using the replacement of the battery as a trigger. Therefore, the data transmission apparatus can advertise the date and time of its own clock unit and the information indicating that these date and time can be used for the association of the date and time in the data receiving apparatus when the information of its own clock unit is reset due to the battery exchange and the association of the date and time needs to be reset in the data receiving apparatus.

According to a seventh aspect of the invention, the sensor data is blood pressure data. Thus, the data transmission apparatus can be used for transmitting blood pressure data.

According to an eighth aspect of the present invention, a data transmission system comprises a data transmission apparatus and a data receiving apparatus for communicating with the data transmission apparatus. The data transmission apparatus includes a first clock unit for indicating a date and time, and a transmitter for transmitting a packet for one-way communication. The packet includes sensor data measured by a sensor and date-and-time difference data indicating a difference between a date and time of the first clock unit at the measurement of the sensor data and a date and time of the first clock unit at the transmission of the packet. The data receiving apparatus includes a second clock unit for indicating a date and time, a receiver for receiving the packet transmitted from the data transmission apparatus, and a calculator for calculating, when the packet is received, date-and-time data indicating a measurement date and time of the sensor data from the date-and-time difference data using the date and time of the second clock unit. Hence, in this data transmission system, the data receiving apparatus can calculate the measurement date and time associated with the sensor data without the date and time association.

According to a ninth aspect of the invention, a data receiving apparatus communicates with a data transmission apparatus. The data receiving apparatus comprises a clock unit for indicating a date and time; a receiver for receiving a packet for one-way communication transmitted from the data transmission apparatus; and a calculator for calculating, when the packet includes sensor data, and date-and-time difference data associated with the sensor data, date-and-time data indicating a measurement date and time of the sensor data from the date-and-time difference data using the date and time of the clock unit. The date-and-time difference data indicates a difference between a local date and time at which the sensor data associated with the date-and-time difference data was measured by the sender of the packet, and a local date and time at which the packet was transmitted by the sender of the packet. Therefore, the data receiving apparatus can calculate the measurement date and time associated with the sensor data without the date and time association as in the first aspect.

According to a tenth aspect of the present invention, a data transmission apparatus comprises a clock unit for indicating a date and time, and a transmitter for transmitting a packet for one-way communication. The packet includes sensor data measured by a sensor, and date-and-time difference data indicating a difference between a date and time of the clock unit at the measurement of the sensor data and a date and time of the clock unit at the transmission of the packet. Therefore, according to the data transmission apparatus, a data receiving apparatus can calculate the measurement date and time associated with the sensor data without the date and time association as in the first aspect.

According to an eleventh aspect of the present invention, the sensor data is blood pressure data. Hence, the data transmission apparatus can be used for transmitting blood pressure data.

The twelfth aspect of the present application is a data structure of a packet for one-way communication transmitted from a data transmission apparatus and received and processed by a data receiving apparatus. The packet includes sensor data, first date-and-time data indicating a local date and time in the data transmission apparatus and associated with the sensor data, and information indicating whether or not the first date-and-time data can be used for date and time association. The data receiving apparatus determines whether or not the first date-and-time data can be used for the date and time association based on the information included in the received packet. If it is determined that the first date-and-time data can be used for the date and time association, the data receiving apparatus performs the process of setting a date and time of a clock unit comprised by itself as a reference date and time, by associating these date and time with the local date and time indicated by the first date-and-time data included in the received packet. Therefore, according to this data structure, the data receiving apparatus can, regardless of whether the local date and time indicated by the first date-and-time data are correct or incorrect, rewrite these local date and time with reference to the date and time indicated by its own clock unit. In addition, the data receiving apparatus resets the association between the reference date and time and the local date and time in the sender of the packet, so that it is possible to prevent the accumulation of errors due to the difference in time counting between its clock unit and a clock unit of the sender of the packet.

The present invention provides a technology enabling a data receiving apparatus to, regardless of whether a date and time associated with sensor data and transmitted from a data transmission apparatus are correct or incorrect, reset these date and time to an appropriate date and time.

BRIEF DESCRIPTION OF THE INVENTION

FIG. 5 is a flowchart showing an operation of a data receiving apparatus according to an embodiment.

FIG. 11 is a figure showing a data structure of a PDU field of an advertisement packet.

FIG. 12 is a figure showing an example of data stored in a payload of a PDU field of a packet received by a data receiving apparatus according to an embodiment.

FIG. 13 is a figure showing a correspondence between a local date and time at the transmitter side and a reference date and time.

FIG. 14 is an explanatory figure of an operation of a date and time calculator of a data receiving apparatus according to an embodiment.

DETAILED DESCRIPTION

Hereinafter, certain embodiment (hereinafter referred to as "present embodiment") according to one aspect of the present invention will be described in detail with reference to the accompanying drawings.

Elements which are the same or similar to once explained elements will be added with the same or similar symbols, and overlapping explanations will be basically omitted.

It is an object of the present embodiments to provide a technology enabling a data receiving apparatus to, regardless of whether or not a date and time associated with sensor data and transmitted from a data transmission device are correct, reset these date and time to an appropriate date and time.

§ 1 Application Example

Figure 1:
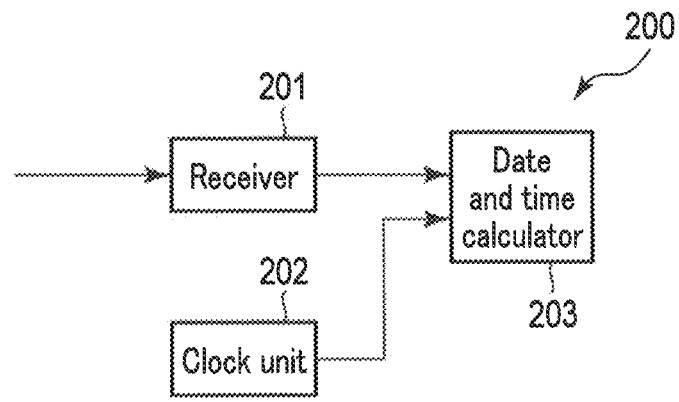
FIG. 1 is a block diagram showing an application example of a data receiving apparatus according to an embodiment.

First, one example of an application of the present invention will be described with reference to FIG. 1. FIG. 1 schematically shows an application example of a data receiving apparatus 200 according to the present embodiment. The data receiving apparatus 200 includes at least a receiver 201, a clock unit 202, and a date and time calculator 203.

The receiver 201 receives a packet including date-and-time data showing a local date and time in a data transmission apparatus 100 (transmission source of a packet) not illustrated in FIG. 1, and sensor data associated with the aforementioned date-and-time data. The receiver 201 sends the date-and-time data and the sensor data to the date and time calculator 203. The clock unit 202 is a built-in clock of the data receiving apparatus 200.

The date and time calculator 203 may refer to the information of a reference date and time, which is the date and time of the clock unit 202 associated with a past specific local date and time in the data transmission apparatus 100. For example, as shown in FIG. 13, it is assumed that the reference date and time="2017/4/1 9:00" is associated with the specific local date and time="100" [minutes].

The date and time calculator 203 converts the local date and time indicated by the received date-and-time data into the date and time of the clock unit 202. Specifically, the date and time calculator 203 can calculate the date and time of the clock unit 202 associated with the local date and time, by adding the difference between the specific local date and time and the local date and time indicated by the received date-and-time data to the reference date and time.

For example, when the local date and time indicates a serial value of "43300" [minutes], the date and time calculator 203 can calculate a date and time of "2017/5/1 9:00" (="2017/4/1 9:00"+"43300" [minutes]−"100" [minutes]) from the serial value. Similarly, as illustrated in FIG. 14, the date and time calculator 203 can rewrite the received date-and-time data using the reference date and time information illustrated in FIG. 13.

As described above, even if the local date and time in the data transmission apparatus 100 is not synchronized, the data receiving apparatus 200 can convert the local date and time into the date and time of its own built-in clock and appropriately handle the sensor data (for example, performing statistical processing, display processing, etc.).

§ 2 Configuration Example

[Hardware Configuration]
<Data Receiving Apparatus>

Figure 4:
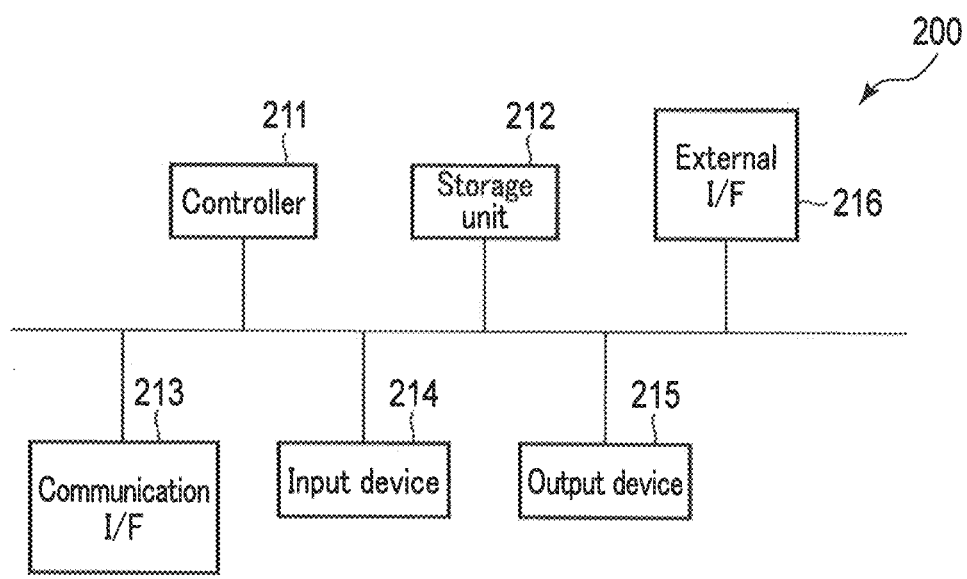
FIG. 4 is a block diagram showing a hardware configuration of a data receiving apparatus according to an embodiment.

Next, an example of hardware configuration of the data receiving apparatus 200 according to the present embodiment is explained using FIG. 4. FIG. 4 schematically shows an example of a hardware configuration of the data receiving apparatus 200.

As shown in FIG. 4, the data receiving apparatus 200 is a computer, typically a smartphone, in which a controller 211, a storage unit 212, a communication interface 213, an input device 214, an output device 215, and an external interface 216 are electrically connected to each other. FIG. 4 describes the communication interface and the external interface as "communication I/F" and "external I/F", respectively.

The controller 211 includes CPU (Central Processing Unit), RAM (Random Access Memory), ROM (Read Only Memory), etc. The CPU loads a program stored in the storage unit 212 to the RAM. Further, the CPU interprets and executes this program so that the controller 211 may execute various information processing, such as executing a function block processing as will be explained in the software configuration section.

The storage unit 212 is a so-called "auxiliary storage" which may be, for example, a semiconductor memory such as an embedded or external flash memory. The storage unit 212 stores a program executed by the controller 211, the data (e.g., identifier, date-and-time data, and sensor data) used by the controller 211, and so on. Further, if the data receiving apparatus 200 is a laptop computer or a desktop computer, the storage unit 212 may be an HDD (Hard Disk Drive) or SSD (Solid State Drive).

The communication interface 213 is a communication module for various wireless communication such as, primarily, BLE, mobile communication (3G, 4G, etc.), and wireless LAN (Local Area Network), and is an interface that performs wireless communication via a network. The communication interface 213 may further comprise a wired communication module, such as a wired LAN module.

The input device 214 is a device for accepting user input (user operational information) such as, e.g., a touch screen, a keyboard, and a mouse. The output device 215 is a device for performing the output, e.g., a display, a speaker or the like.

The external interface 216 is a USB (Universal Serial Bus) port, a memory card slot or the like, and is an interface for connecting with external devices.

Further, with regards to the detailed hardware configuration of the data receiving apparatus 200, the omission, substitution, and addition of features are suitably possible depending on the implementations. In an exemplary instance, the controller 211 may include a plurality of processors. The data receiving apparatus 200 may be configured with a plurality of information processing devices. Further, the data receiving apparatus 200 may be a general-purpose desktop PC (personal computer), tablet PC, etc., or an information processing device designed specifically for the provided service.

<Data Transmission Apparatus>

Figure 7:
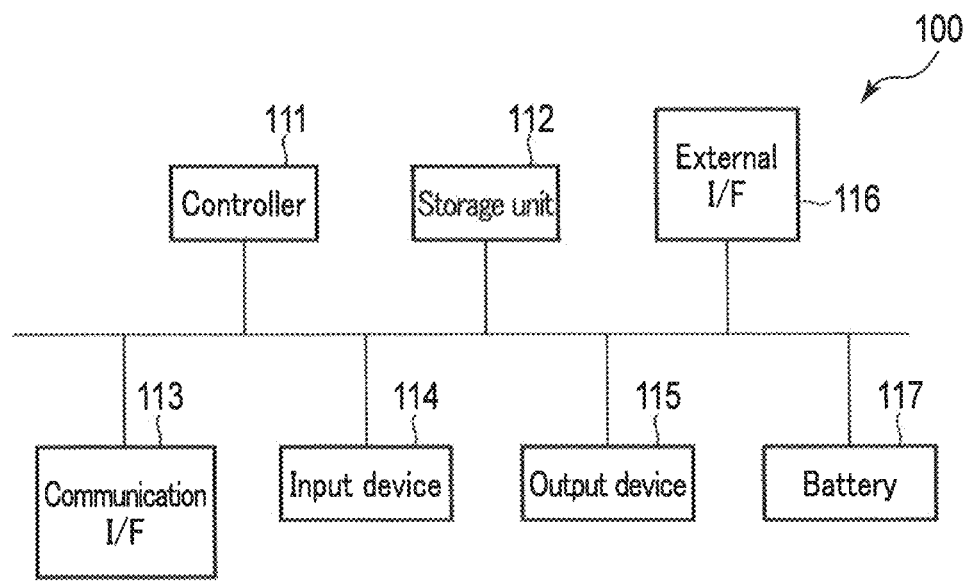
FIG. 7 is a block diagram showing a hardware configuration of a data transmission apparatus according to an embodiment.

Next, an example of a hardware configuration of the data transmission apparatus 100 according to the present embodiment is explained by using FIG. 7. FIG. 7 schematically shows an example of a hardware configuration of the data transmission apparatus 100.

As shown in FIG. 7, the data transmission apparatus 100 is a computer in which a controller 111, a storage unit 112, a communication interface 113, an input device 114, an output device 115, an external interface 116 and a battery 117 are electrically connected to each other, and its typical implementation is a sensor device for measuring, on a daily basis, a quantity related to biological information or activity information of a user, such as a blood pressure monitor, a thermometer, an activity monitor, a pedometer, a body composition monitor, or a weight scale. FIG. 7, respectively, describes the communication interface and the external interface as "communication I/F" and "external I/F."

The controller 111 includes CPU, RAM, ROM, etc. The CPU loads a program stored in the storage unit 112 to the RAM. Further, the CPU interprets and executes this program so that the controller 111 may execute various information processing, such as functional block processing, which will be explained in the software configuration section.

The storage unit 112 is a so-called "auxiliary storage" which may be, for example, a semiconductor memory such as an embedded or external flash memory, an HDD, and an SSD. The storage unit 112 stores a program executed by the controller 111, the data (e.g., date-and-time data, and sensor data) used by the controller 111, and so on.

The communication interface 113 includes a wireless module capable of at least one-way communication such as BLE. The input device 114 includes a device for accepting user input, such as, e.g., a touch screen, a button, and a switch, and a sensor for detecting the quantity related to the user's biological information and activity information. The output device 115 is a device for performing the output, such as a display, a speaker, or the like.

The external interface 116 is a USB port, a memory card slot, etc., and is an interface for connecting with external devices.

The battery 117 supplies power source voltage to the data transmission apparatus 100. The battery 117 may be exchangeable. Further, it is not necessary for the data transmission apparatus 100 to be battery-operated; it may be connected to a commercial power source via an AC (alternating current) adapter. In this case, the battery 117 may be omitted.

Further, with regards to the detailed hardware configuration of the data transmission apparatus 100, the omission, substitutions, and addition of features are suitably possible depending on the implementations. In an exemplary instance, the controller 111 may include a plurality of processors. The data transmission apparatus 100 may be configured with a plurality of sensor devices.

[Software Configuration]
<Data Receiving Apparatus>

Figure 2:
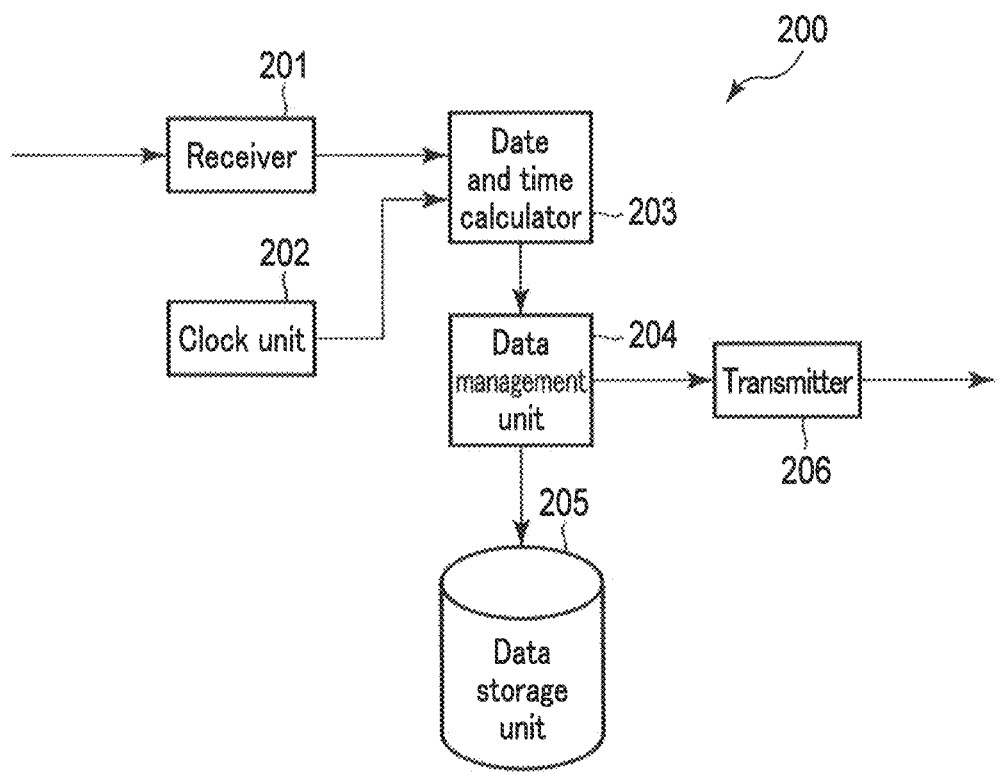
FIG. 2 is a block diagram showing a software configuration of a data receiving apparatus according to an embodiment.

Next, an example of a software configuration of the data receiving apparatus 200 according to the present embodiment is explained using FIG. 2. FIG. 2 schematically shows an example of a software configuration of the data receiving apparatus 200.

The controller 211 shown in FIG. 4 loads the program stored in the storage unit 212 to RAM. Further, the controller 211 using the CPU interprets and executes this program so that the controller 211 may control various hardware elements, illustrated in FIG. 4. As shown in FIG. 2, this allows the data receiving apparatus 200 to function as a computer comprising the receiver 201, the clock unit 202, and the date and time calculator 203, as well as a data management unit 204, a data storage unit 205 and a transmitter 206.

The receiver 201 receives a packet including sensor data and date-and-time data associated with the sensor data from the data transmission apparatus 100. This packet is, for example, an advertisement packet in BLE. However, the BLE may be replaced with another form of a low power consumption, one-way communicable communication standard in the future. In such a case, the following explanation may be suitably reworded.

The following is a schematic explanation regarding a BLE advertisement.

Figure 9:
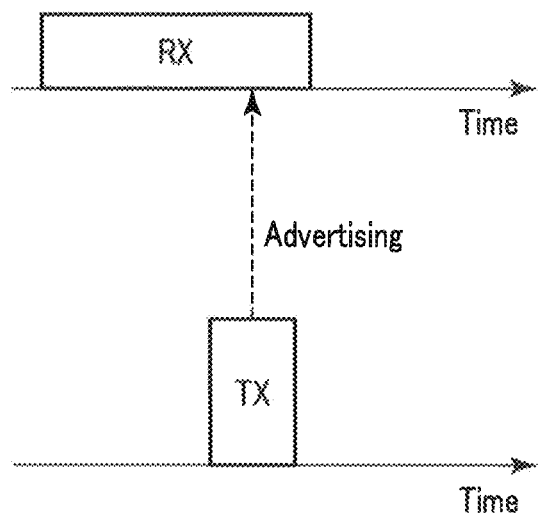
FIG. 9 is an explanatory drawing of advertising performed in BLE.

In the passive scanning method adopted by the BLE, as exemplified in FIG. 9, a new node periodically transmits advertisement packets to publicize the existence of the new node. This new node may reduce power consumption by entering into a sleep state of low power consumption between the times of transmitting an advertisement packet and the next transmission. Furthermore, the reception side of the advertisement packet is also of an intermittent operation; thus, the power consumption for transmission/reception of the advertisement packet is low.

Figure 10:
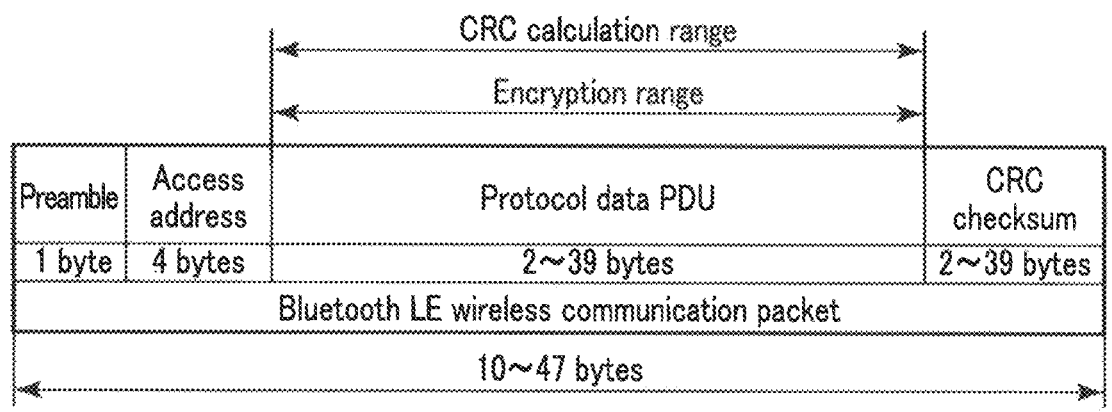
FIG. 10 is a figure showing an example of a data structure of a packet transmitted/received in BLE.

FIG. 10 shows the basic configuration of the BLE wireless communication packet. The BLE wireless communication packet includes a 1-byte preamble, 4-byte access address, 2 to 39-byte (variable) protocol data unit (PDU), and 3-byte cyclic redundancy checksum (CRC). The length of the BLE wireless communication packet is dependent on the length of PDU and is 10-47 bytes. The 10-byte BLE wireless communication packet (PDU is 2 bytes) is called an Empty PDU packet and is periodically exchanged between the master and the slave.

The preamble field is prepared for synchronization of BLE wireless communication, and "01" or "10" is repeatedly stored. The access address stores fixed numerals for the advertising channel, and stores a random number access address for the data channel. The present embodiment targets an advertisement packet which is the BLE wireless communication packet transmitted on the advertising channel. The CRC field is used to detect a reception error. A calculation range of CRC is only the PDU field.

Next, FIG. 11 is used to explain the PDU field of the advertisement packet. Note that the PDU field of the data communication packet, which is the BLE wireless communication packet transmitted on the data channel, has a data structure different from FIG. 11; however, the present embodiment does not target the data communication packet, and the explanation will thus be omitted.

The PDU field of an advertisement packet includes a 2-byte header and a 0 to 37-byte (variable) payload. The header further includes a 4-bit PDU type field, 2-bit unused field, 1-bit TxAdd field, 1-bit RxAdd field, 6-bit Length field, and 2-bit unused field.

The PDU type field stores a value indicating a type of this PDU. Various values, such as the "connectible advertising" and "non-connectible advertising," are already defined. The TxAdd field stores a flag indicating whether or not there is a transmission address in the payload. Similarly, the RxAdd field stores a flag indicating whether or not there is a reception address in the payload. The Length field stores a value indicating the byte size of the payload.

The payload can store desired data. The data transmission apparatus 100 uses the data structure exemplified in, for example, FIG. 12 to store the sensor data and the date-and-time data to the payload. The data structure of FIG. 12 may be used for transmission of one set's worth of sensor data for a blood pressure and pulse of one user. Furthermore, the data structure of FIG. 12 may be modified to transmit multiple sets' worth of sensor data for a blood pressure and pulse of one user.

A user ID field stores an identifier showing a user. Instead of the identifier showing the user, or in addition to such, the identifier showing the data transmission apparatus 100 or the data receiving apparatus 200 may be stored.

A latest flag is a flag (more generally, information) indicating whether or not the date-and-time data stored in a subsequent Time field can be used for the date and time association. When this flag is TRUE, associating the local date and time indicated by the date-and-time data stored in the Time field with the current date and time of the clock unit 202 is allowed.

The Time field stores the date-and-time data. Sys, Dia and Pulse fields respectively store the systolic blood pressure, diastolic blood pressure, and pulse rate data associated with the date-and-time data. The sensor data associated with the date-and-time data is not limited to one type and may be a plurality of types as above.

Returning to the description of the software configuration of the data receiving apparatus 200, the receiver 201, for example, extracts the PDU payload from the BLE advertisement packet. Further, the receiver 201 may discard a received packet if the value in the User ID field of FIG. 12 is unsuitable (for example, if it does not match with the value of its own user). On the other hand, if the value in the User ID field in FIG. 12 is appropriate (it matches the value of the user), the receiver 201 sends a flag stored in the latest flag, the date-and-time data stored in the Time field, and the sensor data stored in the Sys, Dia, and Pulse fields to the date and time calculator 203.

The clock unit 202 indicates a date and time. The clock unit 202 includes, for example, a crystal oscillator which vibrates at a fixed frequency, a frequency divider which obtains 1 Hz signals by dividing an output of the crystal oscillator, and a counter for obtaining a serial value showing a date and time by counting the signals. The clock unit 202 (serial value held by it) may be automatically corrected based on data from a base station to which the data receiving apparatus 200 is connected.

The date and time calculator 203 receives the flag, date-and-time data, and sensor data from the receiver 201. If the flag indicates that the date-and-time data can be used for the date and time association, the date and time calculator 203 associates the current date and time indicated by the clock unit 202 with the local date and time indicated by the date-and-time data as the reference date and time (see FIG. 13).

If such association has been performed in the past, another execution may be omitted. However, if the time count of the clock unit 202 and that of the built-in clock of the data transmission apparatus 100 do not coincide with each other, there is a possibility that a large error will be generated due to accumulation of the difference between them. In order to prevent the accumulation of such errors, it is preferred to reset the association between the reference date and time and the local date and time of the data transmission apparatus 100 as appropriate.

On the other hand, if the flag indicates that the date-and-time data is not available for the date and time association, the date-and-time data is too old compared to the current date and time indicated by the clock unit 202, and thus cannot be associated.

The date and time calculator 203 calculates the difference between the local date and time indicated by the date-and-time data and a local date and time associated with the reference date and time. Then, the date and time calculator 203 adds the difference to the reference date and time to calculate the date and time of the clock unit 202 that is associated with the local date and time indicated by the date-and-time data. The date and time calculator 203 rewrites the date-and-time data based on the calculated date and time (see FIG. 14). The date and time calculator 203 sends the rewritten date-and-time data and the sensor data to the data management unit 204.

The date and time calculator 203 cannot rewrite the date and time until the reference date and time are associated with the local date and time of the data transmission apparatus 100. In order to perform such association, it is necessary to have the data transmission apparatus 100 transmit the (substantially latest) date-and-time data that can be used for the date and time association, and for the data receiving apparatus 200 to receive the data. Therefore, several triggers for causing the data transmission apparatus 100 to transmit the date-and-time data that can be used for the date and time association are ready.

For example, the data transmission apparatus 100 may be adapted so that, immediately after new sensor data is generated by measuring the quantity of the user's biological information, it stores the substantially latest date-and-time data corresponding to a measurement date and time of the sensor data in the advertisement packet of the BLE for transmission. In addition, the data transmission apparatus 100 may store the substantially latest date-and-time data in the advertisement packet of the BLE and transmit the advertisement packet, with a specific user input given by the user as a trigger. Furthermore, the data transmission apparatus 100 may store the substantially latest date-and-time data in the advertisement packet of the BLE and transmit the advertisement packet, with the battery exchange as a trigger. Furthermore, the data transmission apparatus 100 may store the substantially latest date-and-time data in the advertisement packet of the BLE and transmit the advertisement packet, at a predetermined cycle (for example, every 1 day, every 1 week, or the like).

In addition, when the reference date and time and the local date and time of the data transmission apparatus 100 have not been associated with each other at all, or when the elapsed time from the last association exceeds a threshold value, the data receiving apparatus 200 may output text, an image, or a sound prompting a user input, which is one of the triggers.

The data management unit 204 receives the date-and-time data and the sensor data from the date and time calculator 203, and writes them in the data storage unit 205 by associating them with each other. In addition, the data management unit 204 reads a set of the date-and-time data and the sensor data stored in the data storage unit 205 in accordance with the instruction from, e.g., a superior application (not shown) (for example, a management application for biological data), and transmits the read set to the transmitter 206 or a not-illustrated display.

The data storage unit 205 may be subjected to read and write operations by the data management unit 204 for the set of the date-and-time data and the sensor data.

Figure 3:
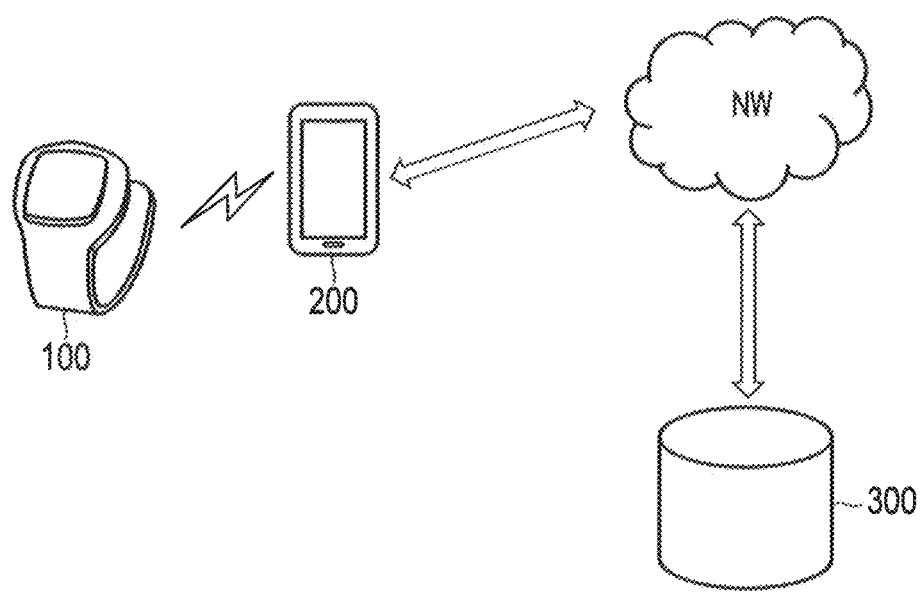
FIG. 3 is a figure showing a data transmission system including a data transmission apparatus and a data receiving apparatus of an embodiment.

The transmitter 206 receives the set of the date-and-time data and the sensor data from the data management unit 204 and transmits it to a server 300 via a network (refer to FIG. 3).

The transmitter 206 uses, for example, mobile communication or WLAN. Note that the example of FIG. 3 shows the exterior of a wristwatch-type wearable blood pressure monitor as the data transmission apparatus 100; however, the exterior of the data transmission apparatus 100 is not limited to the above and may be a stationary blood pressure monitor or a sensor device for measuring the quantity related to other biological information or activity information.

The server 300 corresponds to a database which manages sensor data (mainly, biological data) of various users. The server 300 may transmit biological data of the user, in response to access from the user's personal computer, as well as from, for example, a wellness advisor's, an insurance company's or program operator's PC, etc., to provide health guidance for the user, insurance coverage assessment, and health promotion program evaluation, etc.

<Data Transmission Apparatus>

Figure 6:
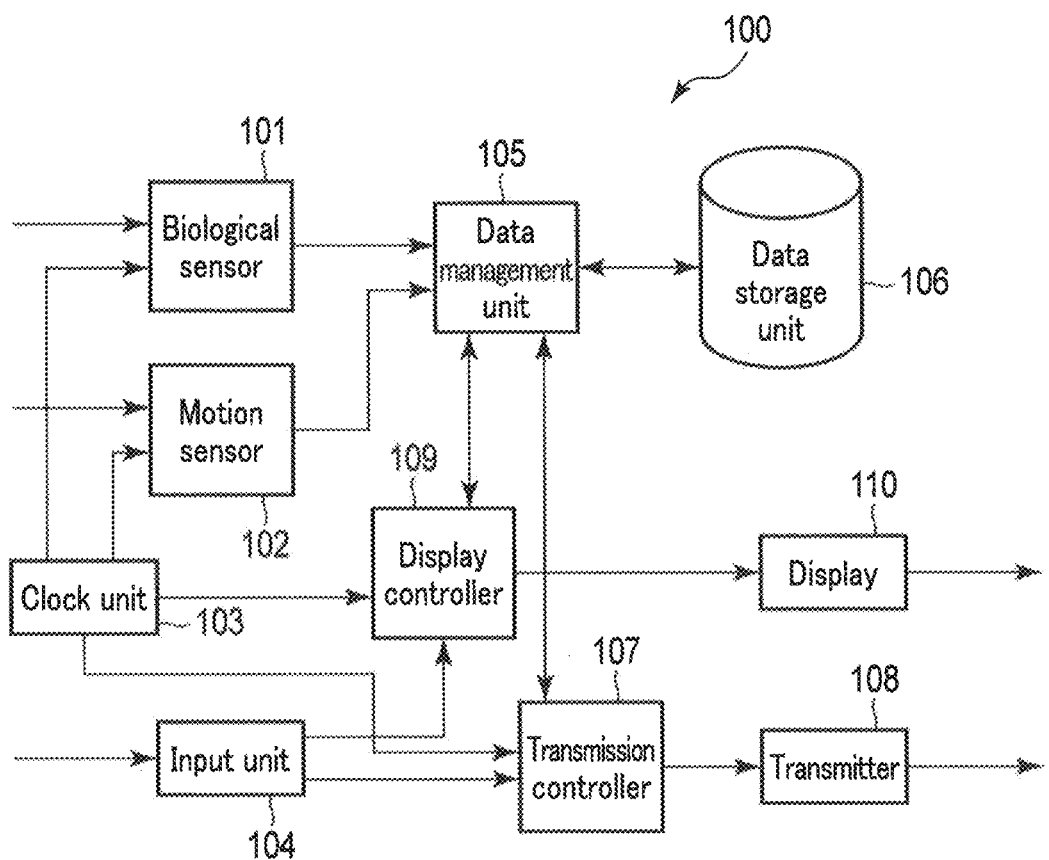
FIG. 6 is a block diagram showing a software configuration of a data transmission apparatus according to an embodiment.

Next, an example of a software configuration of the data transmission apparatus 100 according to the present embodiment is explained by using FIG. 6. FIG. 6 schematically shows an example of a software configuration of the data transmission apparatus 100.

The controller 111 shown in FIG. 7 loads the program stored in the storage unit 112 to RAM. Then, the controller 111 using the CPU interprets and executes this program so that the controller 111 may control various hardware elements, illustrated in FIG. 7. Thus, as shown in FIG. 6, the data transmission apparatus 100 is allowed to function as a computer comprising a biological sensor 101, a motion sensor 102, a clock unit 103, an input unit 104, a data management unit 105, a data storage unit 106, a transmission controller 107, a transmitter 108, a display controller 109, and a display 110.

The biological sensor 101 obtains biological data by measuring the quantity related to the biological information of the user. The operation of the biological sensor 101 is controlled by, for example, a sensor controller (not shown). The biological sensor 101 associates the biological data with the date-and-time data received from the clock unit 103 and sends it to the data management unit 105. The biological sensor 101 typically includes a blood pressure sensor for obtaining blood pressure data by measuring the blood pressure of the user. In this case, the biological data includes the blood pressure data. The blood pressure data may include the values of the systolic blood pressure and the diastolic blood pressure and a pulse rate, but is not limited to the aforementioned. Furthermore, the biological data may include ECG data, pulse wave data, and body temperature data.

The blood pressure sensor may include a blood pressure sensor capable of continuously measuring a blood pressure of a user for each pulse (hereinafter referred to as a "continuous blood pressure sensor"). The continuous blood pressure sensor may continuously measure the blood pressure of a user from a pulse transit time (PTT), but this may be achieved by the tonometry method or other continuous measurement methods.

The blood pressure sensor, instead of the continuous blood pressure sensor or in addition to it, may include a blood pressure sensor incapable of continuous measurements (hereinafter referred to as "non-continuous blood pressure sensor"). The non-continuous blood pressure sensor measures the blood pressure of the user using, for example, a cuff as a pressure sensor (oscillometric method).

The non-continuous blood pressure sensor (in particular, the blood pressure sensor of the oscillometric method) is considered to have high measurement precision compared to the continuous blood pressure sensor. Hence, the blood pressure sensor may measure the blood pressure data with a higher precision by operating the non-continuous blood pressure sensor instead of the continuous blood pressure sensor in response to, for example, the satisfaction of some condition (for example, the blood pressure data of the user measured by the continuous blood pressure sensor suggests a predetermined state) as a trigger.

The motion sensor 102, for example, may be an acceleration sensor or a gyrosensor. The motion sensor 102 obtains three-axis acceleration/angular velocity data by detecting the acceleration/angular velocity received by the motion sensor 102. The operation of the motion sensor 102 is controlled by, for example, a sensor controller (not shown). This acceleration/angular velocity data may be used to estimate an activity status (posture and/or motion) of the user wearing the data transmission apparatus 100. The motion sensor 102 associates the acceleration/angular velocity data with the date-and-time data received from the clock unit 103, and sends it to the data management unit 105.

Further, either one of the biological sensor 101 and the motion sensor 102 may be omitted. Furthermore, an environment sensor may be provided in addition to, or instead of, the biological sensor 101 and motion sensor 102. The environment sensor may include, for example, a temperature sensor, a humidity sensor, and an atmospheric pressure sensor. In other words, the sensor data may be any data generated by a sensor based on a result of its measuring the predetermined physical quantity.

The clock unit 103 indicates a date and time. The clock unit 103 includes, for example, a crystal oscillator which vibrates at a fixed frequency, a frequency divider which obtains 1 Hz signals by dividing an output of the crystal oscillator, and a counter for obtaining a serial value showing a date and time by counting the signals. The clock unit 103 transmits the date-and-time data (for example, the above serial value) showing the current date and time to the biological sensor 101 and motion sensor 102. The date-and-time data may be used as the measurement date and time of the biological data by the biological sensor 101, and as the measurement date and time of the acceleration/angular velocity data by the motion sensor 102 etc. In addition, the date-and-time data is referred to by the display controller 109 for displaying on the display 110. It may also be referred to by the transmission controller 107 for setting the aforementioned flag indicating whether or not the date-and-time data stored in the Time field is available or usable (substantially latest) for the date and time association, or for advertising the available (substantially latest) date-and-time data for the date and time association.

The clock unit 103 (the serial value held by it) may be designed to be adjustable by, for example, user input (time adjustment); nevertheless, as described above, the data receiving apparatus 200 can appropriately rewrite the date-and-time data regardless of whether the local date and time of the data transmission apparatus 100 are correct or incorrect. Therefore, the input device 114 may be simplified (fewer buttons, etc.) by not resorting to such design. In the latter case, it is still possible to present a user with a relative date and time based on the current date and time, such as, "ten minutes before," "two hours before," "yesterday" and "one week before."

The input unit 104 receives a user input. The user input is for controlling data transmission by the transmitter 108, for controlling data display by the display 110, and for starting measurements by the biological sensor 101 or the motion sensor 102.

The user input for controlling data transmission by the transmitter 108 takes the form of, for example, explicitly or implicitly instructing transmission of a set of specific date-and-time data and sensor data and explicitly or implicitly instructing a transmission of the available (substantially latest) date-and-time data for the date and time association.

The input unit 104 sends a user input for controlling data transmission by the transmitter 108 to the transmission controller 107, sends a user input for controlling data display by the display 110 to the display controller 109, and sends a user input for starting measurement by the biological sensor 101 or the motion sensor 102 to the unillustrated sensor controller.

The data management unit 105 receives the sensor data (biological data or acceleration/angular velocity data) associated with the date-and-time data from the biological sensor 101 or motion sensor 102, and writes the data to the data storage unit 106. When the data management unit 105 newly receives the date-and-time data and sensor data, these may be automatically transmitted to the transmission controller 107 or display controller 109. Further, the data management unit 105 may be triggered by the instructions from the transmission controller 107 or display controller 109 so that it reads a set of the date-and-time data and the sensor data stored in the data storage unit 106, and transmits it to the transmission controller 107 or the display controller 109.

The data storage unit 106 is subjected to read and write operations by the data management unit 105 for the set of the date-and-time data and the sensor data.

The transmission controller 107 receives the set of the date-and-time data and the sensor data from the data management unit 105, and generates a BLE advertisement packet as explained using FIGS. 10 to 12. The transmission controller 107 may refer to the date-and-time data held in the clock unit 103 and compare this date-and-time data with the date-and-time data received from the data management unit 105 in order to set a flag indicating whether or not the date-and-time data stored in the Time field can be used for the date and time association. In addition, the transmission controller 107 may receive the (substantially latest) date-and-time data that can be used to associate the date and time from the clock unit 103, and generate based on the received date-and-time data an advertisement packet for advertising the date-and-time data that can be used to associate the date and time, to the data receiving apparatus 200. The transmission controller 107 sends the generated advertisement packet to the transmitter 108.

The transmission controller 107 may receive a user input for controlling data transmission by the transmitter 108 from the input unit 104. In this case, the transmission controller 107 requests a set of specific date-and-time data and sensor data from the data management unit 105 based on the user input, and requests the substantially latest date-and-time data (available for the date and time association) from the clock unit 103. The transmission controller 107 may generate an advertisement packet, regardless of user input, for retransmission of data transmitted in the past and advertising the date-and-time data available for the date and time association.

The transmitter 108 receives the BLE advertisement packet from the transmission controller 107 and transmits (advertises) the packet.

The display controller 109 receives the set of the date-and-time data and the sensor data from the data management unit 105, and generates display data for the display 110 based on the received data set. Further, the display controller 109 may refer to the clock unit 103 to generate display data for displaying the date-and-time data held by the clock unit 103 on the display 110. The display controller 109 sends the generated display data to the display 110.

The display controller 109 may receive a user input for controlling data display by the display 110 from the input unit 104. In this case, the display controller 109 requests a set of specific date-and-time data and sensor data from the data management unit 105 based on the user input and requests the substantially latest date-and-time data from the clock unit 103.

The display 110 receives and displays the display data from the display controller 109.

<Others>

The details regarding each function of the data transmission apparatus 100 and data receiving apparatus 200 will be explained in the operation example below. The present embodiment has assumed the instances where the general-purpose CPU is employed to realize each function of the data transmission apparatus 100 and data receiving apparatus 200. However, a part or of the whole of the discussed functions may be realized by one or a plurality of dedicated processors. Moreover, with regards to the software configurations of the respective data transmission apparatus 100 and data receiving apparatus 200, the omission, substitution, and addition of functions are suitably possible depending on the implementations.

§ 3 Example of Operation

<Data Receiving Apparatus>

Next, an example of an operation of the data receiving apparatus 200 is explained with reference to FIG. 5. FIG. 5 is a flowchart showing an example of the operation of the data receiving apparatus 200. The hereinafter described process is merely an example, and the process may be changed as much as possible. The omission, substitution, and addition of steps in the hereinafter described process are possible as appropriate depending on the implementations.

The operation example of FIG. 5 starts when the receiver 201 of the data receiving apparatus 200 receives a BLE advertisement packet (containing date-and-time data, sensor data, and a flag indicating whether or not the date-and-time data can be used for date and time association) from the data transmission apparatus 100.

First, the date and time calculator 203 refers to the flag received by the receiver 201, and determines whether or not the date-and-time data stored in the advertisement packet can be used for the date and time association (step S401). If the advertisement packet includes the date-and-time data available for the date and time association, the process proceeds to step S402; otherwise, the process proceeds to step S403.

In step S402, the date and time calculator 203 resets the association between the reference date and time and the local date and time of the data transmission apparatus 100. That is, the current date and time indicated by the clock unit 202 is associated with the local date and time indicated by the received date-and-time data, as a reference date and time. Then, the process proceeds to step S404.

In step S403, the date and time calculator 203 determines whether the date and time has been associated, that is, whether the reference date and time has been associated with the local date and time of the data transmission apparatus 100 in the past. If the reference date and time and the local date and time of the data transmission apparatus 100 have been associated with each other in the past, the process proceeds to step S404; otherwise, the process proceeds to step S406.

In step S404, the date and time calculator 203 rewrites the received date-and-time data by using the association between the reference date and time and the local date and time of the data transmission apparatus 100. Specifically, the date and time calculator 203 calculates the difference between the local date and time indicated by the received date-and-time data and the local date and time associated with the reference date and time. Then, the date and time calculator 203 adds the difference to the reference date and time to calculate the date and time of the clock unit 202 that is associated with the local date and time indicated by the date-and-time data. The date and time calculator 203 rewrites the date-and-time data based on the calculated date and time. Then, the process proceeds to step S405.

In step S405, the data management unit 204 associates the date-and-time data rewritten in step S404 with the received sensor data, and stores them into the date storage unit 205, and the process is finished.

In step S406, the date and time calculator 203 cannot rewrite the received date-and-time data since the association between the reference date and time and the local date and time of the data transmission apparatus 100 cannot be used. Therefore, predetermined error processing is performed and the process is finished. This error processing may include, for example, causing the output device 215 of the data receiving apparatus 200 to output text, images, or audio prompting a user input to trigger the data transmission apparatus 100 to advertise date-and-time data available for the date and time association. The received date-and-time data and sensor data may be discarded or saved. If the received date-and-time data and the sensor data are saved, the date-and-time data is rewritten by using the association between the reference date and time and the local date and time of the data transmission apparatus 100, which will be performed later, so that data loss can be prevented.

<Data Transmission Apparatus>

Figure 8:
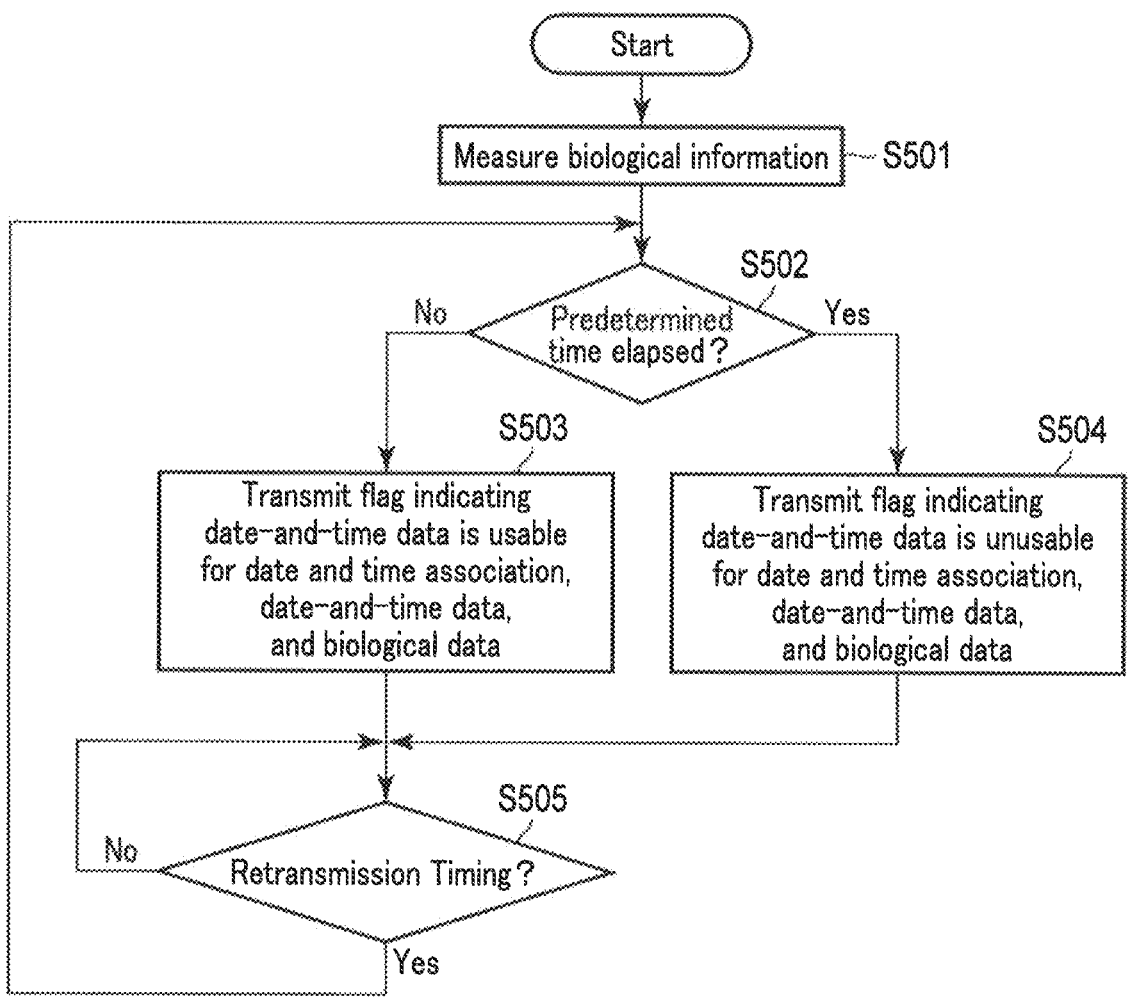
FIG. 8 is a flowchart showing an operation of a data transmission apparatus according to an embodiment.

Next, an operation example of the data transmission apparatus 100 is explained by referring to FIG. 8. FIG. 8 is a flowchart showing an example of an operation of the data transmission apparatus 100. The hereinafter described process is merely an example, and the process may be changed as much as possible. The omission, substitution, and addition of steps in the following process are possible as appropriate depending on the implementations.

The operation example of FIG. 8 starts with the sensor controller (not shown) giving an instruction to the biological sensor 101 to start measurements. Further, regardless of the operation example of FIG. 8, the data transmission apparatus 100 may store the substantially latest date-and-time data (which can be used for the date and time association) of the clock unit 103 in the BLE advertisement packet and transmit the BLE advertisement packet in response to various predetermined triggers. The substantially latest date-and-time data may be transmitted in association with the sensor data, or may be transmitted independently from the sensor data.

The biological sensor 101 measures a quantity of the user's biological information to generate biological data (sensor data) (step S501). This biological data is sent to the data management unit 105 in association with the date-and-time data of the clock unit 103. The data management unit 105 writes a set of the date-and-time data and the biological data in the data storage unit 106, and also sends the data to the transmission controller 107 for advertising. Then, the process proceeds to step S502.

In step S502, the transmission controller 107 compares the date and time indicated by the date-and-time data to be advertised with the current date and time of the clock unit 103, and determines whether or not a predetermined time has elapsed. If the predetermined time has elapsed, the process proceeds to step S504; otherwise, the process proceeds to step S503.

As the predetermined time increases, the accuracy of the association between the reference date and time in the data receiving apparatus 200 and the local date and time of the data transmission apparatus 100 decreases (i.e., the allowable error increases); however, the frequency of the association increases. For example, if the data receiving apparatus 200 manages the measurement time of the sensor data in units of minutes, the predetermined time may be set to several seconds to several tens of seconds.

In step S503, the transmission controller 107 generates an advertisement packet storing a flag indicating that the date-and-time data to be advertised can be used for the date and time association, the date-and-time data, and the biological data measured in step S501, and the transmitter 108 transmits the advertisement packet. Then, the process proceeds to step S505.

Alternatively, in step S504, the transmission controller 107 generates an advertisement packet storing a flag indicating that the date-and-time data to be advertised cannot be used for the date and time association, the date-and-time data, and the biological data measured in step S501, and the transmitter 108 transmits (advertises) the packet. Then, the process proceeds to step S505.

In step S505, the retransmission timing of the advertisement packet transmitted in step S503 or step S504 is awaited. In a one-way communication such as the transmission of an advertisement packet, since a transmission source cannot check whether the transmission data has been correctly received by the destination, it is preferable to retransmit the data assuming that the data is missing at the destination. When the retransmission timing arrives, the process returns to step S502.

According to the loop from step S502 to step S505, the advertisement packet including the flag indicating that the date-and-time data to be advertised can be used for the date and time association is repeatedly transmitted until a predetermined time elapses from the measurement of the quantity related to the biological information (step S501). That is, if the data receiving apparatus 200 receives the advertisement packet before the predetermined time elapses, the data receiving apparatus 200 can associate the reference date and time with the local date and time of the data transmission apparatus 100.

Advantageous Effects

As explained above, in the present embodiment, the data transmission apparatus transmits a packet for one-way communication including date-and-time data indicating the substantially latest date-and-time data (which can be used for the date and the time association) of a clock unit, in response to a predetermined trigger. Then, the data receiving apparatus associates the date and time indicated by the date-and-time data transmitted from the data transmission apparatus with the current date and time (reference date and time) of its own built-in clock unit. Thereafter, the data receiving apparatus rewrites the local date and time of the data transmission apparatus, indicated by the date-and-time data associated with the sensor data transmitted from the data transmission apparatus, based on the date and time indicated by the own built-in clock unit. Therefore, according to the present embodiment, the data receiving apparatus can calculate an appropriate date and time associated with the sensor data even when the time of the clock unit embedded in the data transmission apparatus is not adjusted or this clock unit indicates an inaccurate date and time.

§ 4 Modifications

Although the embodiment of the present invention has been described in detail in the foregoing, the description is merely an example of the present invention in every respects. Various improvements and modifications can, of course, be made to the embodiment without deviating from the scope of the present invention. The following modifications may be made for example. In the following, the same reference numerals are used for the same constituent elements of the foregoing embodiment, and redundant descriptions are omitted as appropriate. The following modifications may be combined as appropriate.

<4.1>

In an exemplary instance of the above embodiment, the data transmission apparatus stores sensor data and date-and-time data indicating a measurement date and time of the sensor data in a BLE advertisement packet and transmits the BLE advertisement packet. However, the data transmission apparatus may store date-and-time difference data indicating an elapsed date and time from the measurement date and time, instead of the date-and-time data indicating a measurement date and time of the sensor data, into a BLE advertisement packet and transmit the BLE advertisement packet. The date-and-time difference data can be derived, for example, by calculating a difference between the (measurement) date and time indicated by the date-and-time data associated with the sensor data and the substantially latest date and time of the clock unit 103 (i.e., at the time of packet transmission).

In this modification, the data receiving apparatus calculates the date-and-time data from the date-and-time difference data using the substantially latest date and time of the clock unit 202. Specifically, the date and time calculator 203 can calculate the date and time associated with the sensor data by subtracting the difference indicated by the date-and-time difference data from the substantially latest date and time of the clock unit 202.

According to this modification, it is necessary to calculate the date-and-time difference data each time the data transmission apparatus 100 transmits the sensor data; however, the data receiving apparatus 200 can calculate the date and time associated with the sensor data without associating the reference date and time with the local date and time of the data transmission apparatus 100.

Note that the above-explained embodiment is only an example of the present invention in all aspects. Various improvements and modifications can, of course, be made to it without deviating from the scope of the present invention. Thus, when the present invention is implemented, a concrete structure depending on the implementations may be suitably adopted. Further, the data introduced in each embodiment has been explained by natural language; however, more specifically, the data items are specified by pseudolanguage, commands, parameters, machine language, etc. recognized by a computer.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

§ 5 Additional Note

A part of or all of each embodiment above may also be described as in the following additional notes, aside from the scope of claims, without limitation thereto.

(Additional Note 1)

A data receiving apparatus which communicates with a data transmission apparatus, the data receiving apparatus comprising:
a memory; and
a processor connected to the memory;
wherein the processor is configured to function as:
(a) a clock unit which indicates a date and time,
(b) a receiver which receives a packet for one-way communication transmitted from the data transmission apparatus, and
(c) a calculator which (1) stores, in a memory, a date and time indicated by the clock unit and associated with a local date and time indicated by first date-and-time data as a reference date and time, when the packet includes the first date-and-time data indicating the local date and time in the data transmission apparatus and information indicating that the first date-and-time data can be used for date and time association, and (2) calculates third date-and-time data based on a difference between the local date and time stored in the memory and associated with the reference date and time and a local date and time indicated by second date-and-time data, and on the reference date and time stored in the memory, when the packet includes sensor data, and the second date-and-time data indicating the local date and time in the data receiving apparatus and associated with the sensor data.

(Additional Note 2)

A data transmission apparatus, comprising:
a memory; and
a processor connected to the memory;
wherein the processor is configured to function as:
(a) a clock unit which indicates a date and time, and
(b) a transmitter which transmits (1) a first packet for one-way communication including first date-and-time data indicating a date and time of the clock unit, and information indicating that the first date-and-time data is available for date and time association, and (2) a second packet for one-way communication including sensor data measured by a sensor and second date-and-time data which indicates the date and time of the clock unit at measurement of the sensor data.

(Additional Note 3)

A data receiving apparatus which communicates with a data transmission apparatus, the data receiving apparatus comprising:
a memory; and
a processor connected to the memory;
wherein the processor is configured to function as:
(a) a clock unit which indicates a date and time,
(b) a receiver which receives a packet for one-way communication transmitted from the data transmission apparatus, and
(c) a calculator which calculates date-and-time data showing a measurement date and time of sensor data from date-and-time difference data using the date and time of the clock unit when the packet includes the sensor data and the date-and-time difference data associated with the sensor data,
wherein the date-and-time difference data indicates a difference between a local date and time at which a transmission source of the packet measured the sensor data associated with the date-and-time difference data and a local date and time at which the transmission source of the packet transmitted the aforementioned packet.

(Additional Note 4)

A data transmission apparatus comprising:
a memory; and
a processor connected to the memory;
wherein the processor is configured to function as:
(a) a clock unit which indicates a date and time,
(b) a transmitter which transmits a packet for one-way communication, wherein
the packet includes sensor data measured by a sensor and date-and-time difference data indicating a difference between a date and time of the clock unit at measurement of the sensor data and a date and time of the clock unit at transmission of the packet.

What is claimed is:

1. A data transmission system comprising:
a data transmission apparatus; and
a data receiving apparatus which communicates with the data transmission apparatus, wherein
the data transmission apparatus comprises:
a first clock unit indicative of a date and time; and
a transmitter configured to transmit (1) a first packet for one-way communication, the first packet including first date-and-time data and information, the first date-and-time data being indicative of a first date and time of the first clock unit, the information being indicative of the first date-and-time data which is available for date and time association, and (2) a second packet for one-way communication, the second packet including sensor data and second date-and-time data, the sensor data being measured by a sensor, the second date-and-time data showing a second date and time of the first clock unit at measurement of the sensor data, and
the data receiving apparatus comprises:
a second clock unit indicative of a date and time;
a receiver configured to receive the first packet and the second packet transmitted from the data transmission apparatus; and
a calculator configured to (1) store, in response to receipt of the first packet, the first date and time and a third date and time indicated by the second clock unit in a memory, the third date and time being associated with the first date and time of the first clock unit indicated by the first date-and-time data, the third date and time being stored as a reference date and time, and (2) calculate, in response to receipt of the second packet, third date-and-time data based on a difference between the first date and time stored in the memory and the second date and time indicated by the second date-and-time data, and based on the reference date and time stored in the memory.

2. A data receiving apparatus which communicates with a data transmission apparatus, the data receiving apparatus comprising:
  a clock unit which indicates a date and time;
  a receiver configured to receive a first packet and a second packet for one-way communication transmitted from the data transmission apparatus; and
  a calculator configured to (1) store, in response to the first packet including first date-and-time data indicative of a first local date and time in the data transmission apparatus and information indicating that the first date-and-time data is available for date and time association, the first local date and time and the date and time indicated by the clock unit in a memory, the date and time being associated with the first local date and time indicated by the first date-and-time data, the date and time being stored as a reference date and time, and (2) calculate, in response to the second packet including sensor data and second date-and-time data indicative of a second local date and time in the data transmission apparatus and associated with the sensor data, third date-and-time data based on a difference between the first local date and time stored in the memory and the second local date and time indicated by the second date-and-time data, and based on the reference date and time stored in the memory.

3. A data transmission apparatus comprising:
  a clock unit indicative of a date and time; and
  a transmitter configured to transmit (1) a first packet for one-way communication, the first packet including first date-and-time data and information, the first date-and-time data being indicative of a first date and time of the clock unit, the information being indicative of the first date-and-time data which is available for date and time association, and (2) a second packet for one-way communication, the second packet including sensor data and second date-and-time data, the sensor data being measured by a sensor, the second date-and-time data indicative of a second date and time of the clock unit at measurement of the sensor data,
  wherein a data receiving apparatus is configured to (1) store, in response to receipt of the first packet, the first date and time and a third date and time indicated by the second clock unit in a memory, the third date and time being associated with the first date and time of the first clock unit indicated by the first date-and-time data, the third date and time being stored as a reference date and time, and (2) calculate, in response to receipt of the second packet, third date-and-time data based on a difference between the first date and time stored in the memory and the second date and time indicated by the second date-and-time data, and based on the reference date and time stored in the memory.

4. The data transmission apparatus according to claim 3, wherein the transmitter is configured to transmit a third packet including the sensor data, the first date-and-time data indicative of the date and time of the clock unit at the measurement of the sensor data, and information indicative of the first date-and-time data being available for date and time association, before a predetermined time elapses from a measurement date and time of the sensor data, and transmit a fourth packet including the sensor data, the second date-and-time data indicative of the date and time of the clock unit at the measurement of the sensor data, and information indicative of the second date-and-time data being unavailable for date and time association, after the predetermined time elapses from the measurement date and time of the sensor data.

5. The data transmission apparatus according to claim 3, further comprising:
  an input unit configured to receive an input of operational information of a user,
  wherein the transmitter is configured to transmit the first packet including the first date-and-time data indicative of the date and time of the clock unit, using a part of the operational information as a trigger.

6. The data transmission apparatus according to claim 3, wherein the data transmission apparatus is operated by a battery, and
  the transmitter is configured to transmit the first packet including the first date-and-time data indicative of the date and time of the clock unit, using battery exchange as a trigger.

7. The data transmission apparatus according to claim 3, wherein the sensor data is blood pressure data.

8. A data transmission system, comprising:
  a data transmission apparatus; and
  a data receiving apparatus which communicates with the data transmission apparatus, wherein
  the data transmission apparatus comprises:
    a first clock unit indicative of a date and time; and
    a transmitter configured to transmit a packet for one-way communication,
  wherein the packet includes sensor data measured by a sensor, and date-and-time difference data indicative of a difference between a date and time of the first clock unit at measurement of the sensor data and a date and time of the first clock unit at transmission of the packet,
  the data receiving apparatus comprises:
    a second clock unit indicative of a date and time;
    a receiver configured to receive the packet transmitted from the data transmission apparatus; and
    a calculator configured to calculate, in response to receipt of the packet, date-and-time data indicative of a measurement date and time of the sensor data from the date-and-time difference data using the date and time of the second clock unit.

9. A data receiving apparatus which communicates with a data transmission apparatus, the data receiving apparatus comprising:
  a clock unit indicative of a date and time;
  a receiver configured to receive a packet of one-way communication transmitted from the data transmission apparatus, the packet including sensor data and date-and-time difference data associated with the sensor data; and
  a calculator configured to calculate, in response to the packet, date-and-time data indicative of a measurement date and time of the sensor data from the date-and-time difference data using the date and time of the clock unit,
  wherein the date-and-time difference data is indicative of a difference between a local date and time at which the sensor data associated with the date-and-time difference data was measured by a transmission source of the packet and a local date and time at which the transmission source of the packet transmitted the packet.

10. A non-transitory computer readable medium storing instructions to cause a processor to transmit a packet for one-way communication from a data transmission apparatus; and/or receive and process the packet by a data receiving apparatus, wherein:

the packet includes sensor data, first date-and-time data and information, the first date-and-time data being indicative of a first local date and time in the data transmission apparatus and associated with the sensor data, the information being indicative of whether the first date-and-time data is available for date and time association, and the data receiving apparatus performs a process that comprises:

determining whether or not the first date-and-time data is available for the date and time association based on the information included in the received packet, setting a date and time of a clock unit comprised by the data receiving apparatus as a reference date and time by associating the date and time of the clock unit with the first local date and time indicated by the first date-and-time data included in the received packet, if the first date-and-time data is determined to be available for the date and time association, and calculating, in response to receipt of the packet, date-and-time data indicative of a measurement date and time of the sensor data from a date-and-time difference data using the date and time of the clock unit, date-and-time difference data being indicative of a difference between the first local date and time at measurement of the sensor data and a second local date and time in the data transmission apparatus at transmission of the packet.

* * * * *